United States Patent
Mearns Spragg

(10) Patent No.: US 11,485,772 B2
(45) Date of Patent: Nov. 1, 2022

(54) MODIFIED COLLAGEN, METHODS OF MANUFACTURE THEREOF

(71) Applicant: JELLAGEN PTY LTD, Stirling—Central Scotland (GB)

(72) Inventor: Andrew Mearns Spragg, Stirling—Central Scotland (GB)

(73) Assignee: JELLAGEN PTY LTD

( * ) Notice: Subject to any disclaimer, the term of this patent is extended or adjusted under 35 U.S.C. 154(b) by 674 days.

(21) Appl. No.: 15/565,817

(22) PCT Filed: Apr. 12, 2016

(86) PCT No.: PCT/GB2016/051025
§ 371 (c)(1),
(2) Date: Oct. 11, 2017

(87) PCT Pub. No.: WO2016/166524
PCT Pub. Date: Oct. 20, 2016

(65) Prior Publication Data
US 2018/0118809 A1 May 3, 2018

(30) Foreign Application Priority Data
Apr. 13, 2015 (GB) ..................... 1506236

(51) Int. Cl.
| | |
|---|---|
| *C07K 14/78* | (2006.01) |
| *A61L 26/00* | (2006.01) |
| *A61K 38/01* | (2006.01) |
| *A61L 15/42* | (2006.01) |
| *A61K 35/614* | (2015.01) |
| *A61L 15/44* | (2006.01) |
| *A61L 15/32* | (2006.01) |
| *A61L 15/46* | (2006.01) |
| *A61K 38/00* | (2006.01) |

(52) U.S. Cl.
CPC ............ *C07K 14/78* (2013.01); *A61K 35/614* (2013.01); *A61K 38/014* (2013.01); *A61L 15/325* (2013.01); *A61L 15/425* (2013.01); *A61L 15/44* (2013.01); *A61L 15/46* (2013.01); *A61L 26/008* (2013.01); *A61L 26/0033* (2013.01); *A61L 26/0066* (2013.01); *A61L 26/0085* (2013.01); *A61K 38/00* (2013.01); *A61L 2300/404* (2013.01)

(58) Field of Classification Search
CPC .... A61K 35/614; A61K 38/00; A61K 38/014; A61L 15/325; A61L 15/425; A61L 15/44; A61L 15/46; A61L 2300/404; A61L 26/0033; A61L 26/0066; A61L 26/008; A61L 26/0085; A61P 17/02; A61P 31/00; C07K 14/78
See application file for complete search history.

(56) References Cited

U.S. PATENT DOCUMENTS

| | | |
|---|---|---|
| 6,660,280 B1 | 12/2003 | Allard et al. |
| 2009/0099337 A1 | 4/2009 | Otagiri |
| 2010/0285102 A1* | 11/2010 | Angel ................ A61L 15/40 424/445 |
| 2013/0116189 A1 | 5/2013 | Tanihara |

FOREIGN PATENT DOCUMENTS

| | | | |
|---|---|---|---|
| JP | 2001/009020 | 1/2001 | |
| JP | 2004099513 | 4/2004 | |
| JP | 2009057318 | 8/2007 | |
| JP | 2008/212026 | 9/2008 | |
| JP | 2012240984 | 12/2012 | |
| WO | 2005092362 | 10/2005 | |
| WO | WO-2006095193 A2 * | 9/2006 | ......... A61L 26/0066 |
| WO | 2011158864 | 6/2010 | |

OTHER PUBLICATIONS

Proteomic Analysis of S-Nitrosylated Proteins in Mesangial Cells, Molecular & Cellular Proteomics 2.3, pp. 156-162, 2003.*
Michael VanWagner, S-Nitroso-N-acetylpenicillamine (SNAP) Derivatization of Peptide Primary Amines to Create Inducible Nitric Oxide Donor Biomaterials, ACS Appl. Mater. Interfaces 2013, 5, 8430-8439.*
Sourour Addad, Isolation, Characterization and Biological Evaluation of Jellyfish Collagen for Use in Biomedical Applications, Mar. Drugs 2011, 9, 967-983.*
Teresa Kuncewicz, Proteomic Analysis of S-Nitrosylated Proteins in Mesangial Cells, Molecular & Cellular Proteomics 2.3, 2003.*
Ruba Deeb, Untargeted Discovery of Nitric Oxide-Modified Proteins, Nitric Oxide: Biology and Pathobiology, second edition, chapter 10, 2009.*
Yasui et al., Dual-site recognition of different extracellular matrix components by anti-angiogenic/neurotrophic serpin, PEDF, Biochemistry, 2003, vol. 42, pp. 3160-3167.
Byler D M, Gosser D K, Susi H, Spectroscopic Estimation of the Extent of S. Nitrosothiol Formation by Nitrite Action on Sulfhydryl-Groups,Journal of Agricultural and Food Chemistry, 1983, vol. 31, 523-527.
Wink D A, Nims R W, Darbyshire J F, et al., Reaction-Kinetics for Nitrosation of Cysteine and Gluathione in Aerobic Nitric-Oxide Solutions at Neutral ph—Insights into the Fate and Physiological-Effects of Intermediates Generated in the no/0-2 Reaction, Chemical Research in Toxicology, 1994, vol. 7: 519-525.
Norihisa Yasui et al: Collagen-Protein Interactions Mapped by Phototriggered Thiol Introduction, Journal of the American Chemical Society, Dec. 1, 2003, pp. 15728-15729, vol. 125, No. 51, XP055280316.
Michele C. Jen et al: Polymer-Based Nitric Oxide Therapies: Recent Insights for Biomedical Applications, Advanced Functional Materials, Nov. 17, 2011, pp. 239-260, vol. 22, No. 2, XP055280371.

(Continued)

*Primary Examiner* — Julie Ha
*Assistant Examiner* — Erinne R Dabkowski
(74) *Attorney, Agent, or Firm* — Dickinson Wright PLLC

(57) ABSTRACT

The present invention provides a modified collagen comprising S-nitroso groups and a method of manufacture of such a modified collagen. Also provided is a wound dressing comprising such a modified collagen, particularly a wound dressing comprising a formulated composition comprising such a modified collagen.

16 Claims, 2 Drawing Sheets

(56) References Cited

OTHER PUBLICATIONS

Figure 1:
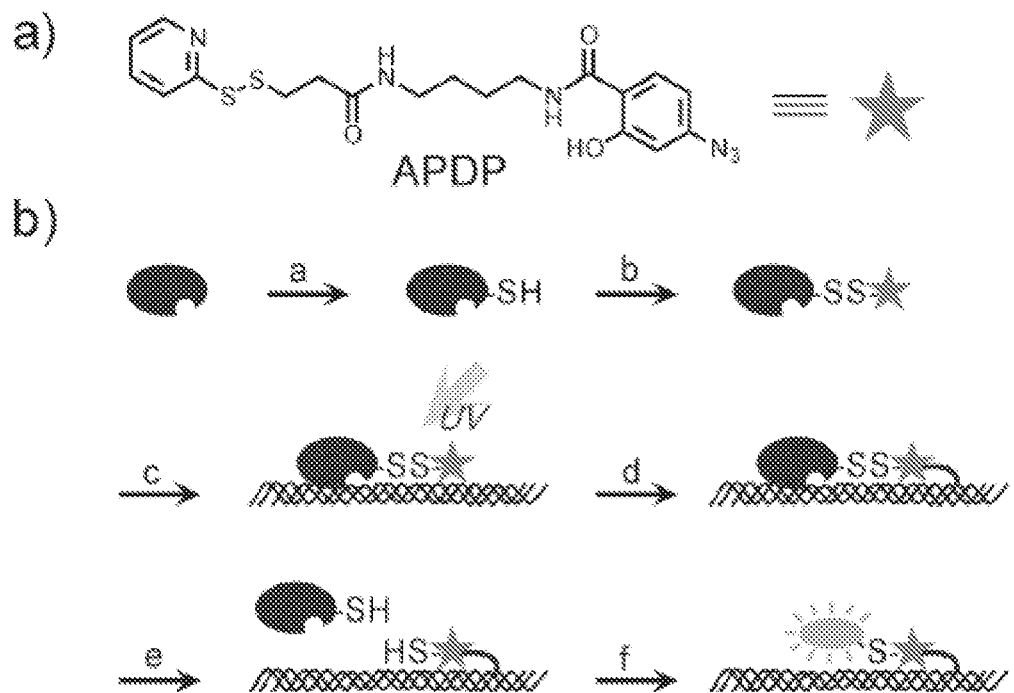
Figure 1:
Figure 1:
Figure 1:
Figure 1:

Shefaat Ullah Shah et al; Synthesis and characterization of S-nitrosoglutathione-oligosaccharide-chitos an as a nitric oxide donor, Expert Opinion on Drug Delivery, Mar. 24, 2015, pp. 1209-1223, vol. 12, No. 8, XP055226668.

George Han et al: Nitric Oxide-Releasing Nanoparticles Accelerate Wound Healing by Promoting Fibroblast, Migration and Collagen Deposition, American Journal of Pathology, Apr. 1, 2012, pp. 1465-1473, vol. 180, No. 4, XP055280218.

Hosur N. Achuth et al: Nitrosoglutathione triggers collagen deposition in cutaneous wound repair, Wound Repair and Regeneration, Jul. 1, 2005, pp. 383-389, vol. 13, No. 4, XP055280539.

International Search Report, for International Application No. PCT/GB2016/051025; dated Apr. 12, 2016.

International Preliminary Report on Patentability for International Application No. PCT/GB2016/051025; dated Apr. 12, 2016.

Written Opinion of the International Searching Authority for International Application No. PCT/GB2016/051025; dated Apr. 12, 2016.

Dilullo et al., Mapping the Ligand-binding Sites and Disease-associated Mutations on the Most Abundant Protein in the Human, Type I Collagen, J. Biol. Chem. 2002, 277(6): 4223-4231.

Zecherle et al., The C-Terminal Doman of *Escherichia coli* Ribosomal Protein L7/L12 Can Occupy a Location near the Factor-Binding Domain of the 50S Subunit as Shown by Cross-Linking with N-[4- (p-Azidosalicylamido)butyl]-3-(2'-pyridyldithio) propionamide, Biochem. 1992, 31(40): 9526-9532.

Fiber and Industry, Collagen as Derived Fibrous Protein—its Character and Application 65: 2009, 453-461.

Miller MR, Recent developments in nitric oxide donor drugs, British Journal of Pharmacology, 2007, 305-321, 151, Nature Publishing Group.

Nicolas F L, Denatured thiolated collagen. I Synthesis and characterization, Biomaterials, 1997, 807-13, 18, PubMed.Gov.

Schairer DO, The potential of nitric oxide releasing therapies as antimicrobial agents, Europe PMC, May 1, 2012, 271-279, 3, Virulence.

Yasui Norihisa, Dual-Site Recognition of Different Extracellular Matrix Componenents by Anti-Angiogenic/Neurotrophic Serpin, PEDF, Biochemistry, 2003. Biochem., 3160-3167, 42, American Chemical Society.

Baysal, Nitric Oxide II: Therapeutic Uses and Clinical Applications; Turk J Med Sci 32 (2002) 1-6.

Simon, Antiplatelet properties of protein S-nitrosothiols derived from nitric oxide and endothelium-derived relaxing factor; Journal of the American Heart Association; Arterioscler Thromb Vasc Biol. 1993;13:791-799.

Shunji Hattori, Collagen as an Animal Derived Fibrous Protein—Its Character and Application, Fiber and industry 2009, 453-461, vol. 65, No. 12, Sen'I Gakkaishi.

* cited by examiner

Key:

represents a collagen-binding protein;

represents a cysteine-containing collagen-binding protein, showing the sulfhydryl group of the cysteine;

represents collagen; and represents a S-nitroso group.

MODIFIED COLLAGEN, METHODS OF MANUFACTURE THEREOF

CROSS-REFERENCE TO RELATED APPLICATIONS

The present application is a 35 U.S.C. Section 371 national stage filing of International Patent Application No. PCT/GB2016/051025, filed 12 Apr. 2016, and through which priority is claimed to United Kingdom Patent Application GB 1506236.7, filed 13 Apr. 2015, the disclosures of which are incorporated herein by reference in their entireties.

FIELD OF INVENTION

The present invention provides a method for the manufacture of a modified collagen molecule having one or more of vasodilative, anti-inflammatory and disinfection effects. More specifically, the present invention relates to a modified collagen which can be formulated with one or both of other collagen species and other polymers to fabricate films, membranes, hydrogels and other constructs capable of producing stable gel or membrane based scaffolds for application as a wound healing medical device.

BACKGROUND TO THE INVENTION

Collagen is the major protein of the extracellular matrix (ECM) and is the most abundant protein found in mammals, comprising 25% of the total protein content and 70% to 80% of skin (dry weight). The central feature of all collagen molecules is their stiff, triple-stranded helical structure. Types I, II, and III are the main types of collagen found in connective tissue and constitute 90% of all collagen in the body.

Previously, collagens were thought to function only as a structural support; however, it is now evident that collagen and collagen-derived fragments control many cellular functions, including cell shape and differentiation, migration, and synthesis of a number of proteins. Findings suggest that cell contact with precise extracellular matrix molecules influence cell behaviour by regulating the quantity and quality of matrix deposition.

Wound healing is a complex process that involves coordinated interactions between diverse immunological and biological systems. Long-term wounds remain a challenging clinical problem, affecting approximately 6 million patients per year, with a high economic impact.

Wound healing is a process whereby the skin (or another organ-tissue) repairs itself after injury. In normal skin, the epidermis (outermost layer) and dermis (inner or deeper layer) exist in a steady-state equilibrium and shielded from the external environment. When the skin is broken, the normal (physiologic) process of wound healing begins. The classic model of wound healing comprises three or four sequential, yet overlapping, phases:

Phase 1: Haemostasis.
Phase 2: Inflammation.
Phase 3: Proliferation.
Phase 4: Remodelling.

Upon injury to the skin, a set of complex biochemical events takes place in a closely orchestrated cascade to repair the damage. Due to a number of potential stimuli (local tissue ischaemia, bioburden, necrotic tissue, repeated trauma, etc.), wounds can stall in the inflammatory phase contributing to the chronicity of the wound. One key component of chronic wounds is an elevated level of matrix metalloproteinases (MMPs). At elevated levels, MMPs not only degrade nonviable collagen but also viable collagen. In addition, fibroblasts in a chronic wound may not secrete tissue inhibitors of MMPs (TIMPs) at an adequate level to control the activity of MMPs. These events prevent the formation of the scaffold needed for cell migration and ultimately prevent the formation of the extracellular matrix (ECM) and granulation tissue.

Collagen-based wound dressings are uniquely suited to address the issue of elevated levels of MMPs by acting as a 'sacrificial substrate' in the wound. It has also been demonstrated that collagen breakdown products are chemotactic for a variety of cell types required for the formation of granulation tissue. In addition, collagen based dressings have the ability to absorb wound exudates and maintain a moist wound environment.

A number of different collagen dressings are available, which employ a variety of carriers/combining agents such as gels, pastes, polymers, oxidized regenerated cellulose (ORC), and ethylene diamine tetraacetic acid (EDTA). The collagen within these products tends to be derived from bovine, porcine, equine, or avian sources, which is purified in order to render it nonantigenic. The collagen in a given collagen dressing can vary in concentration and type. Certain collagen dressings are comprised of Type I (native) collagen; whereas, other collagen dressings contain denatured collagen (gelatine) as well. A given collagen dressing may contain ingredients, such as alginates and cellulose derivatives that can enhance absorbency, flexibility, and comfort, and help maintain a moist wound environment.

Research has shown that some collagen-based dressings produce a significant increase in the fibroblast production; have a hydrophilic property that may be important in encouraging fibroblast permeation; enhance the deposition of oriented, organized collagen fibres by attracting fibroblasts and causing a directed migration of cells; aid in the uptake and bioavailability of fibronectin; help preserve leukocytes, macrophages, fibroblasts, and epithelial cells; and assist in the maintenance of the chemical and thermostatic microenvironment of the wound. The mode of action of several collagen dressings includes the inhibition or deactivation excess MMPs. As mentioned, excess MMPs are a key contributor to wound chronicity.

Collagen dressings have a variety of pore sizes and surface areas as well. All of these attributes are designed to enhance the wound management aspects of the dressings. Many collagen dressings contain an antimicrobial agent to control pathogens within the wound. Collagen dressings typically require a secondary dressing.

NO is a volatile gas produced in many tissues and organs of the body, which acts as a signalling mechanism between cells. NO exerts several effects including:

Vasodilation.
Stimulation of angiogenesis.
Regulation of immune responses.
Potent anti-microbial activity.

In recent years, NO has emerged as a critical molecule in wound healing, with NO levels increasing rapidly after skin damage and gradually decreasing as the healing process progresses. In a study by Han G et al. titled "Nitric Oxide-Releasing Nanoparticles Accelerate Wound Healing by Promoting Fibroblast Migration and Collagen Deposition", The American Journal of Pathology. 2012; Vol. 180, No. 4, April, the authors demonstrated the effects of a novel NO-releasing nanoparticle technology on wound healing in mice. The results showed that the NO-nanoparticles (NO-np) were able to significantly accelerate wound healing. It was also found that the NO-np was able to modify leukocyte migration and increase the production of tumour growth factor-β in the wound area, which subsequently promoted angiogenesis (blood flow) to enhance the healing process. The authors also demonstrated that using human dermal fibroblasts, the NO-np increased fibroblast migration and collagen deposition in wounded tissue. This data shows that NO-releasing nanoparticles have the ability to modulate and accelerate wound healing in a pleiotropic manner.

While NO-nanoparticles have demonstrated that it should be feasible to deliver a localised NO effect, the ability to create collagen-NO scaffolds as a method of developing wound care devices has not been demonstrated.

The clinical use of NO to date has been minimal, mainly due to the technical challenge of delivering it effectively to target tissues and also being able to store the NO in a stable form in materials. Additional technical challenges of NO include being able to release the molecule from a medical device at the correct rate (kinetics) for its particular use.

In diabetic foot ulcer wounds, a combination of the associated chronic microbial infection and inflammation can lead to blood capillary degradation (reduced blood flow) and amputation. It is desirable for a medical device targeting diabetic foot ulcers (DFU) to:

Provide clinical benefits in reducing the associated infection.

Provide the ability to stimulate blood flow to the affected region.

Promote wound healing.

Meet the growing market demand for safer more efficacious products for treatment of DFU.

The present invention seeks to meet the problems outlined above through development of a S-nitroso collagen to deliver exogenous NO, particularly a S-nitroso collagen based scaffold, such as a S-nitroso collagen I, II, III, IV, V, VI, IX X or XI based scaffold derived from either mammalian or marine sources and more preferably from jellyfish. The benefits of this technology are the production of a localised and controlled release of nitric oxide (NO) to help stimulate blood flow and also the treatment of microbial infection associated with DFU. Current therapeutic strategies have proved suboptimal in the treatment of DFU and it is imperative to focus on new therapeutic approaches and the development of technologies for both short and long-term wound management.

This invention provides NO release systems for wound care involving the synthesis of modified collagen comprising S-nitroso groups.

S-Nitrosothiols, also called thionitrites, may serve as carriers in the mechanism of action of endothelium relaxing factor (EDRF) by stabilising the labile NO radical from inactivation by reactive oxygen species and thus delivering Nitric Oxide to the site of wound damage causing increased blood flow and effective treatment of the microbial infection.

The ability to supply exogenous NO is advantageous because it restores the body's natural defence and signalling system.

SUMMARY OF INVENTION

In a first aspect of the invention, there is provided a method of producing a modified collagen, comprising at least the steps of:

providing a collagen comprising a S—S bond;

introducing a —SH group in said collagen comprising a S—S bond by reduction of the S—S bond to provide a collagen thiol comprising a —SH group;

nitrosating the —SH group of the collagen thiol to provide a modified collagen, said modified collagen comprising S-nitroso groups.

In one embodiment, the collagen is preferably collagen of one or more of Type I, II, III, IV, V, VI, IX, X and XI. In another embodiment, the collagen is a collagen other than collagen of one or more of Type I, II, III, IV, V, VI, IX, X and XI, such as collagen of one or more of Type VII, VIII, XII, XIII, XIV, XV, XVI, XVII, XVIII, XIX, XX, XXI, XXII, XXIII, XXIV, XXV, XXVI, XXVII, XXVIII and XXIX.

In one embodiment, the collagen is preferably one or more of Type I, II and V. In another embodiment, the collagen is preferably one or more of Type IV and XI like materials.

In one embodiment, the step of providing a collagen comprising a S—S bond, comprises at least the steps of:

providing a source collagen comprising one or both of lysine and hydroxylysine residues;

reacting the source collagen with an activated dicarboxylic acid derivative comprising a disulphide group to form amide bonds between the carbonyl function of the activated dicarboxylic acid derivative and the ε-$NH_2$ groups of one or both of the lysine and hydroxylysine residues, thereby providing the collagen comprising a S—S bond.

In another embodiment, the source collagen is one or more of Type I, II, III, IV, V, VI, IX, X and XI, said source collagen comprising one or both of lysine and hydroxylysine residues and the collagen comprising the S—S bond is one or more of Type I, II, III, IV, V, VI, IX, X and XI comprising a S—S bond.

In another embodiment, the source collagen is selected from one or both of pepsin solubilised collagen and acid solubilised collagen, preferably pepsin solubilised collagen.

In another embodiment, the activated dicarboxylic acid derivative is a compound of the formula:

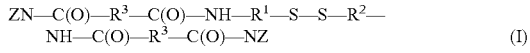

wherein $R^1$, $R^2$ and $R^3$ independently represent divalent linking groups; and ZN together represent a nitrogen containing heterocyclic group.

In another embodiment, the activated dicarboxylic acid derivative comprises the compound:

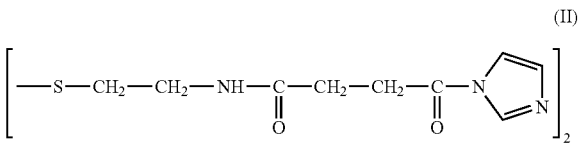

In another embodiment, the step of providing a collagen comprising a S—S bond, comprises at least the steps of:

providing a collagen-binding protein wherein the collagen-binding protein comprises a cysteine residue comprising —SH groups;

reacting the cysteine residue —SH groups of the collagen-binding protein with a photoreactive cross-linker to provide a photoreactive cross-linker modified collagen-binding protein comprising a S—S group;

combining the photoreactive cross-linker modified collagen-binding protein with a collagen to provide a complex of the photoreactive cross-linker modified collagen-binding protein and the collagen;

irradiating the complex with electromagnetic radiation to cross-link the photoreactive cross-linker with the collagen to provide the collagen comprising a S—S bond.

In another embodiment, the collagen comprising the S—S bond is one or more of Type I, II, III, IV, V, VI, IX, X and XI comprising a S—S bond.

In another embodiment, the step of providing the collagen-binding protein comprising a cysteine residue is carried out by site-directed mutagenesis of a collagen-binding protein.

In another embodiment, the photoreactive cross-linker is N-[4-(p-azidosalicylamido)butyl]-3'-(2'pyridyldithio) propionamide (APDP) and the electromagnetic radiation is ultraviolet radiation.

In another embodiment, the S-nitroso groups are in the vicinity of a protein binding site on the modified collagen.

In another embodiment, the step of introducing a —SH group in said collagen comprising a S—S bond by reduction of the S—S bond to provide a collagen thiol having a —SH group comprises:

reacting the collagen comprising a S—S bond with dithiothreitol.

In another embodiment, the nitrosating of the —SH group comprises one or more of:

reacting the —SH group of the collagen thiol with a solution of acidified nitrite;

reacting the —SH group of the collagen thiol with gaseous NO; and reacting the —SH group of the collagen thiol with a S-nitrosothiol.

In another embodiment, the nitrosating of the —SH group is carried out in the presence of a chelating agent, such as EDTA.

In another embodiment, the nitrosating of the —SH group is carried below room temperature, such as a temperature of less than 5° C., preferably a temperature of less than 0° C.

In another embodiment, the method further comprises the step of:

incorporating the modified collagen into a one or more of the group comprising a type II collagen, a type V collagen and a gelatin matrix; or incorporating the modified collagen into a polymer, preferably a film-forming polymer, a membrane-forming polymer, a hydrogel-forming polymer or a polymer that is able to fabricate films, membranes, hydrogels and other constructs capable of producing stable gel or membrane based scaffolds.

In another embodiment, the collagen, particularly a collagen of one or more of Type I, II, III, IV, V, VI, IX, X and XI, is derived from mammalian or non-mammalian sources, such as natural or GMO sources.

In another embodiment, the non-mammalian source is one or more selected from jellyfish, marine invertebrate and fish.

In another embodiment, the collagen, such as the collagen derived from a non-mammalian source, is atelocollagen.

In a second aspect, there is provided a modified collagen obtainable by the method of the first aspect or its embodiments.

In a third aspect, there is provided a modified collagen comprising S-nitroso groups.

In one embodiment, the modified collagen is preferably derived from collagen of one or more of Type I, II, III, IV, V, VI, IX, X and X. In another embodiment, the collagen is a collagen other than collagen of one or more of Type I, II, III, IV, V, VI, IX, X and XI, such as collagen of one or more of Type VII, VIII, XII, XIII, XIV, XV, XVI, XVII, XVIII, XIX, XX, XXI, XXII, XXIII, XXIV, XXV, XXVI, XXVII, XXVIII and XXIX.

In one embodiment, the modified collagen is derived from mammalian or non-mammalian sources, such as natural or GMO sources.

In another embodiment, the non-mammalian source from which the modified collagen is derived is one or more selected from jellyfish, marine invertebrate and fish.

In another embodiment, the modified collagen is derived from atelocollagen. The atelocollagen may be produced by pepsin enzyme digestion of a source collagen.

In another embodiment, the modified collagen comprising S-nitroso groups comprises a lysine or hydroxylysine residue of formula (IX):

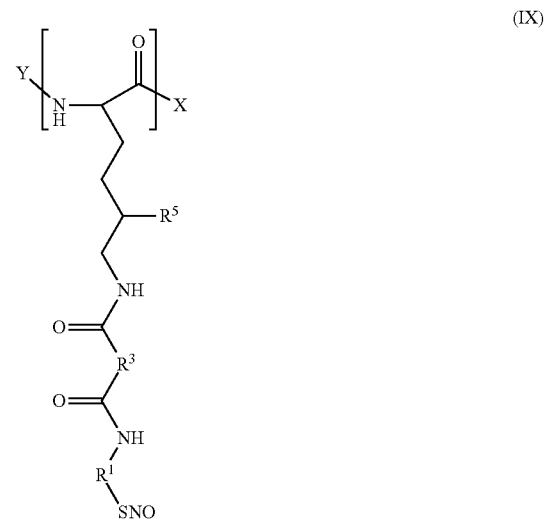

(IX)

in which $R^1$ and $R^3$ are as defined above, and preferably independently represent ethanediyl or propanediyl groups, most preferably ethanediyl i.e. —$CH_2CH_2$—;

$R^5$ is H or OH;

X is selected from the group OH or a chemical bond; and

Y is selected from H or a chemical bond, with the proviso that one or both of X and Y are chemical bonds forming peptide bonds within the modified collagen.

In a fourth aspect, the modified collagen is for use as a medicament.

In one embodiment, the modified collagen is for use in wound healing.

In another embodiment, the wound healing is the treatment of a wound, preferably an ulcer, more preferably a diabetic ulcer, particularly a diabetic foot ulcer.

In a fifth aspect, there is provided a wound dressing comprising a formulated composition comprising the modified collagen incorporated into one or more of the group comprising a type II collagen derived from a jellyfish, a type V collagen derived from a jellyfish and a gelatin matrix.

In a sixth aspect, there is provided a wound dressing comprising a formulated composition comprising the modified collagen incorporated into a polymer based matrix scaffold comprising of either chondroitin, hyaluronic acid, silicon, or some other polymer based technology applicable for wound application.

In one embodiment of the wound dressing, the formulated composition is a film, membrane or hydrogel composite.

In another embodiment of the wound dressing, said film, membrane or hydrogel composite has a thickness in a range of from 5 to 200 micrometer.

In another embodiment of the wound dressing, said film, membrane or hydrogel composite is sterilised, preferably during formation of the wound dressing.

In another embodiment of the wound dressing, said film, membrane or hydrogel composite has a porous structure.

In another embodiment of the wound dressing, said collagen derived from a jellyfish comprises Rhizostoma pulmo jellyfish tissue.

In another embodiment of the wound dressing, it further comprises food grade agents.

In another embodiment of the wound dressing, it further comprises medical grade agents.

In another embodiment of the wound dressing, it has enhanced vasodilation effects, particularly with respect to blood flow control.

In another embodiment of the wound dressing, it acts as a disinfection agent.

In another embodiment of the wound dressing, it has antimicrobial properties, particularly against bacteria, yeasts, fungi and viruses.

In a seventh aspect, there is provided a method of S-nitrosation of the —SH-containing groups within collagen thiol comprising one or more of exposure to nitric oxide (NO) delivered from acidified nitrite, exposure to NO gas and reaction with a S-nitrosothiol.

In one embodiment, the modified collagen is treated with an excess of a S-nitrosothiol.

In another embodiment, the S-nitrosothiol is one or more selected from the group comprising S-nitroso-glutathione, S-nitroso-N-acetylpenicillamine and S-nitroso-cysteine.

FIGURES

Embodiments of the present invention will now be described, by way of example only, with reference to the accompanying figures in which:

FIG. 1a) shows the structure of a photoreactive cross-linker, N-[4-(p-azidosalicylamido)butyl]-3'-(2'pyridyldithio) propionamide (APDP), which can be used in the method disclosed herein.

FIG. 1b) shows a scheme for one method of introducing sulfhydryl groups into a collagen as disclosed herein.

Figure 2:
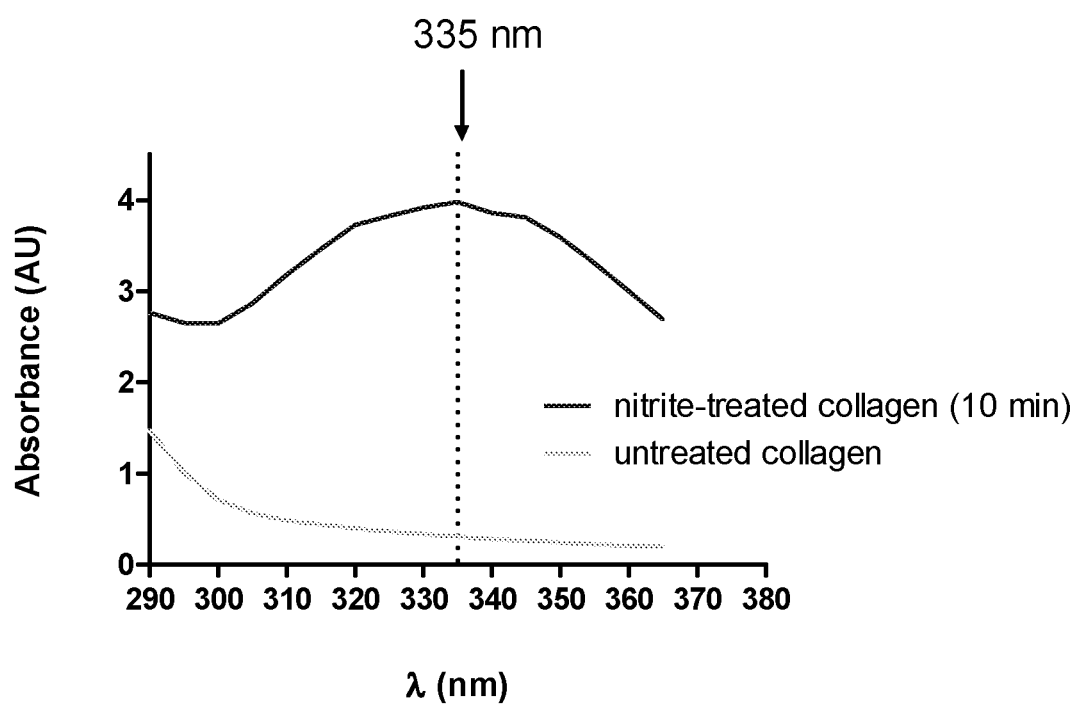

FIG. 2 shows the absorption spectrum in the wavelength range of 290 to 365 nm of a modified collagen comprising a S—H group after 10 minutes treatment with a nitrosating agent together with a control sample to which no nitrosating agent was added, as detailed in the Example below.

DETAILED EXAMPLES OF THE INVENTION

In the following detailed description, numerous specific details are set forth in order to provide a thorough understanding of the present invention. It will be understood by those of ordinary skill in the art that embodiments of the present invention may be practiced without these specific details while still remaining within the scope of the claims.

Type I collagen is the most abundant structural component of the dermal matrix and migrating keratinocytes likely interact with this protein. Collagenase (via the formation of gelatin) may aid in dissociating keratinocytes from collagen-rich matrix and thereby promote efficient migration over the dermal and provisional matrices.

Cellular functions are regulated by the extracellular matrix (ECM). The information provided by ECM macromolecules is processed and transduced into the cells by specialized cell surface receptors. Evidence demonstrates that the receptors play a major function in contraction of wounds, migration of epithelial cells, collagen deposition, and induction of matrix-degrading collagenase. Although keratinocytes will adhere to denatured collagen (gelatin), collagenase production is not turned on in response to this substrate. Keratinocytes have been known to recognize and migrate on Type I collagen substratum, resulting in enhanced collagenase production. Collagen therefore plays a key role in each phase of wound healing.

The present invention relates to a method of producing a modified collagen comprising S-nitroso groups. Sulfhydryl (—SH) groups in proteins represent an abundant source of reduced thiol for interaction with NO and S-nitroso-proteins which form readily under physiological conditions. The major limitation to determining protein-binding sites on collagen has been a lack of useful methods for introducing such sulfhydryl groups.

The modified collagen described herein may be produced from collagen of one or more of Type I, II, III, IV, V, IX and X, also referred to herein as "source" collagen. The modified collagen may be produced from collagen derived from mammalian or non-mammalian sources. Preferably, when the collagen is derived from mammalian sources, it is derived from non-human mammalian sources. The non-mammalian source may be one or more source selected from jellyfish, marine invertebrate and fish. The modified collagen may be produced from collagen derived from natural or genetically modified organism (GMO) sources.

The first step of the method described herein comprises providing a collagen in which the collagen comprises a S—S bond. Preferably the collagen is one or more of Type I, II, III, IV, V, VI, IX, X and XI. Alternatively the collagen is collagen other than one or more of Type I, II, III, IV, V, VI, IX, X and XI, such as collagen of one or more of Type VII, VIII, XII, XIII, XIV, XV, XVI, XVII, XVIII, XIX, XX, XXI, XXII, XXIII, XXIV, XXV, XXVI, XXVII, XXVIII and XXIX.

Naturally occurring collagen does not typically comprise a S—S bond. Disulphide groups may be incorporated into collagen by a number of routes. In a preferred embodiment, the collagen comprising a S—S bond is obtainable by providing a source collagen, in which the collagen comprises one or both of lysine and hydroxylysine residues. For instance, the source collagen may be collagen of one or more of Type I, II, III, IV, V, VI, IX, X and XI having one or both of lysine and hydroxylysin residues.

Lysine and hydroxylysine are α-amino acids having ε-amino groups. As used herein, the term "residue" refers to the portion of a chemical compound remaining after incorporation into, for instance by chemical reaction and bond formation, another substance. Thus, amino acid "residue" refers to the polymerised form of an amino acid monomer present in a polypeptide. Collagen is formed of a triple-helix of polypeptide chains, one or more of which commonly comprise one or both of lysine and hydroxylysine residues. Lysine is present as one of the ten most abundant amino acid residues in both mammalian and fish collagen. Although 4-5 times less plentiful in collagen than lysine residue, hydroxylysine residue is also present in amounts sufficient to be of use in the method disclosed herein. Thus, a collagen comprising a lysine or hydroxylysine residue, prior to treatment as described herein, may comprise a residue of formula (XI):

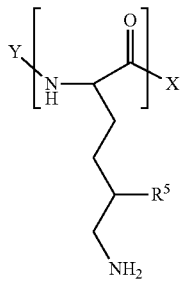

in which R⁵ is H or OH. When R⁵ is H a lysine residue is present. When R⁵ is OH a hydroxylysine residue is present; and X is selected from the group OH and a chemical bond and Y is selected from H and a chemical bond, with the proviso that one or both of X and Y are chemical bonds forming peptide bonds within collagen. The peptide chain forming part of the modified collagen is shown bracketed by "[ ]" in formula (XI). The residue could be in a terminal position of the peptide, for instance if one or other of X and Y is OH and H respectively. If both X and Y are peptide bonds, the lysine residue is non-terminal within the peptide chain forming part of the collagen.

The source collagen comprising one or both of lysine and hydroxylysine residues is preferably solubilised source collagen comprising one or both of lysine and hydroxylysine. The solubilisation may be achieved by pepsin digestion or acid digestion to provide pepsin solubilised source collagen comprising one or both of lysine and hydroxylysine or by acid digestion to provide acid solubilised source collagen comprising one or both of lysine and hydroxylysine.

The source collagen, such as a pepsin solubilised or acid solubilised source collagen, comprising one or both of lysine and hydroxylysine residues, can be reacted with an activated dicarboxylic acid derivative comprising a disulphide (i.e. S—S) group to provide collagen comprising a S—S bond, such as collagen of one or more of Type I, II, III, IV, V, VI, IX, X and XI comprising a S—S bond. In this reaction, the carbonyl group of the activated dicarboxylic acid derivative can react with the ε-amino group of the lysine or hydroxylysine residues present in the collagen to form an amide bond.

The activated dicarboxylic acid derivative is preferably a compound of the formula:

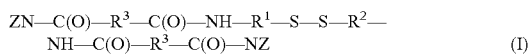

wherein $R^1$, $R^2$ and $R^3$ independently represent divalent linking groups, preferably divalent organic linking groups, more preferably divalent hydrocarbon linking groups, such as an alkanediyl group having from 1 to 6 carbon atoms or alkendiyl or alkyndiyl groups having from 2 to 6 carbon atoms. Still more preferably, $R^1$, $R^2$ and $R^3$ independently represent ethanediyl or propanediyl groups, most preferably ethanediyl i.e. —CH₂CH₂—. The groups $R^1$, $R^2$ and $R^3$ may independently be optionally substituted by replacing one to four hydrogen atoms with a hydroxyl group or a halogen, such as F or Cl. In a preferred embodiment, $R^1$ and $R^2$ are identical; and ZN together represent a nitrogen containing heterocyclic group, preferably a nitrogen containing heterocyclic group having 5-6 atoms in the heterocyclic ring, in which the N atom is directly bonded to the carbonyl group of the compound of formula (I) such that Z represents a divalent linking group in which the two valences are bonded to the nitrogen. The heterocyclic group may be saturated or unsaturated, such that Z may represent an alkanediyl, alkendiyl or alkyndiyl, particularly having 2 to 4 carbon atoms. Z may optionally comprise 1 or 2 heteroatoms selected from O, S and N. More preferably, ZN is a nitrogen containing heteroaryl group having 5-6 atoms in the aryl ring of which from 1-3 atoms are heteroatoms selected from O, N and S at least 1 of which is N which is directly bonded to the carbonyl group of the compound of formula (I). Still more preferably the heteroaryl group has 5-6 atoms in the aryl ring of which 2 atoms are N. Alternatively, ZN is a nitrogen containing heterocyclic group having 5-6 atoms in the heterocyclic ring having 1 N atom which is directly bonded to the carbonyl group of the compound of formula (I) and Z is a α, ω-organodionediyl. For example, the α, ω-organodionediyl may be represented as —C(O)R⁴C(O)— in which R⁴ is an alkanediyl or alkendiyl having from 2 or 3 carbon atoms.

The group ZN may be optionally substituted by replacing from one to four hydrogen atoms with a hydroxyl group or a halogen, such as F, Br or Cl or by replacing two hydrogen atoms bonded to the same carbon with an oxygen atom to form a carbonyl group, wherein the latter substitution may occur once or twice.

Most preferably, the group ZN is:

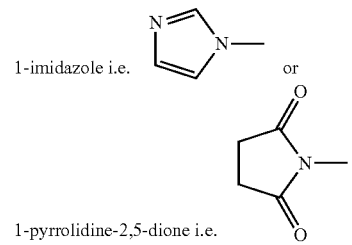

Preferred activated dicarboxylic acid derivatives may be selected from:

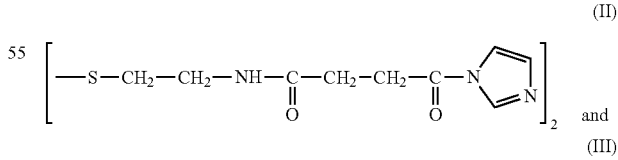

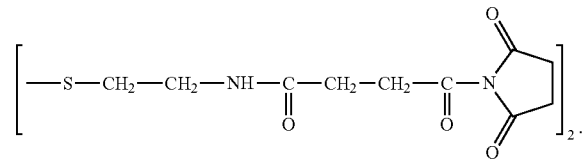

The activated dicarboxylic acid derivative (I) may be synthesised in two steps. Firstly, a diamino disulphide of formula (IV) may be reacted with at least two molar equivalents of a dicarboxylic acid anhydride of formula (V) to provide a dicarboxylic acid diamide of formula (VI):

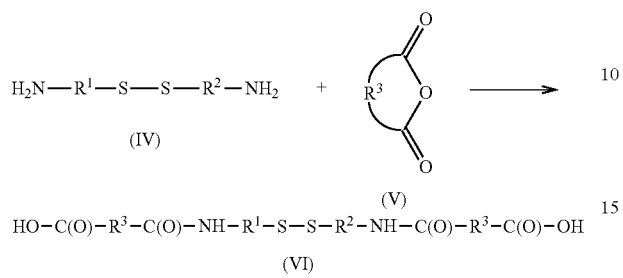

(IV)

(V)

HO—C(O)—R$^3$—C(O)—NH—R$^1$—S—S—R$^2$—NH—C(O)—R$^3$—C(O)—OH (VI)

in which R$^1$, R$^2$ and R$^3$ are as defined above. It will be apparent that when R$^1$ and R$^2$ are identical, the diamino disulphide of formula (IV) is a symmetrical molecule, which will result in a symmetrical activated dicarboxylic acid derivative (I).

The first reaction step may be carried out by dissolving the diamino disulphide of formula (IV) in a solvent, such as water, and adding the dicarboxylic acid anhydride of formula (V). It is preferred that the reaction is carried out under basic conditions, such that prior to the addition of the acid anhydride, a base can be added. For instance, aqueous sodium hydroxide can be added to adjust the pH to 10. After addition of the dicarboxylic acid anhydride, the pH may decrease, and it is preferred to maintain the pH in the range of from 7 to 10 during the reaction by the addition of further base. The reaction may be carried out at room temperature under stirring and may be complete within 30 minutes to 2 hours. The dicarboxylic acid diamide product of formula (VI) may be precipitated by lowering the pH, for instance to a pH of 1, by the addition of acid, such as aqueous hydrochloric acid. The precipitated dicarboxylic acid diamide (VI) can be isolated by filtration, washed with water and then dried under reduced pressure.

In the second step of the synthesis the dicarboxylic acid diamide (VI) is activated by the addition of a nitrogen containing heterocyclic compound to provide the activated dicarboxylic acid derivative (I):

HO—C(O)—R$^3$—C(O)—NH—R$^1$—S—S—R$^2$—NH—C(O)—R$^3$—C(O)—OH(VI)→ZN—C(O)—R$^3$—C(O)—NH—R$^1$—S—S—R$^2$—NH—C(O)—R$^3$—C(O)—NZ    (I)

in which R$^1$, R$^2$, R$^3$ and NZ are as defined above.

In one embodiment, the nitrogen containing heterocyclic compound may be a carbodiimide, such as a compound of formula (VII):

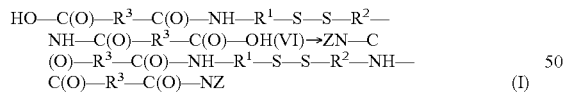

(VII)

in which Z is as defined above. Preferably, ZN together are a nitrogen containing heteroaryl group having 5-6 atoms in the aryl ring of which from 1-3 atoms are heteroatoms selected from O, N and S at least 1 of which is N. The carbodiimide (VII) is more preferably 1,1'-carbonyl-diimidazole or the like.

At least 2 molar equivalents of the carbodiimide should be used per mole of dicarboxylic acid diamide (VI). Theoretically, the reaction will produce 2 molar equivalents of carbon dioxide and 2 molar equivalents of imidazole, per mole of dicarboxylic acid diamide (VI). The evolution of carbon dioxide gas indicates that the reaction is proceeding. The reaction may be carried out under reduced pressure.

In another embodiment, the nitrogen containing heterocyclic compound may be a N-hydroxy heterocyclic compound of formula (VIII):

(VIII)

in which ZN together is a nitrogen containing heterocyclic group having 5-6 atoms in the heterocyclic ring of which 1 is N and Z is a α, ω-organodionediyl. For example, the α, ω-organodionediyl may be represented as —C(O)R$^4$C(O)— in which R$^4$ is an alkanediyl or alkenediyl having from 2 or 3 carbon atoms. The N-hydroxy heterocyclic compound (VIII) is most preferably N-hydroxy succinimide.

The second reaction step may be carried out by dissolving the dicarboxylic acid diamide (VI) in a solvent, such as anhydrous dimethylformamide and then adding the nitrogen containing heterocyclic compound (VII) or (VIII). The activated dicarboxylic acid derivative (I) precipitates from the solution. The product can be collected by filtration, washed with anhydrous ethyl acetate, and dried under reduced pressure.

Returning to the first step of the method of the invention, a source collagen comprising one or both of lysine and hydroxylysine residues can be reacted with an activated dicarboxylic acid derivative comprising a disulphide group, such as the activated dicarboxylic acid derivative of formula (I) to provide collagen comprising a S—S bond, such as collagen of one or more of Type I, II, III, IV, V, VI, IX, X and XI comprising a S—S bond. In this reaction, a carbonyl group of the activated dicarboxylic acid derivative can react with the ε-amino group of the lysine or hydroxylysine residues present in the collagen to form an amide bond, thereby incorporating the disulphide group. The reaction can be represented by:

ZN—C(O)—R$^3$—C(O)—NH—R$^1$—S—S—R$^2$—NH—C(O)—R$^3$—C(O)—NZ(I)+collagen-NH$_2$→ZN—C(O)—R$^3$—C(O)—NH—R$^1$—S—S—R$^2$—NH—C(O)—R$^3$—C(O)—NH-collagen+HNZ This reaction may continue to provide a cross-linked collagen when both activated carboxyl groups of the activated dicarboxylic acid derivative react with collagen, particularly different collagen triple helices or fibrils:

ZN—C(O)—R$^3$—C(O)—NH—R$^1$—S—S—R$^2$—NH—C(O)—R$^3$—C(O)—NH-collagen+collagen-NH$_2$→Collagen-HN—C(O)—R$^3$—C(O)—NH—R$^1$—S—S—R$^2$—NH—C(O)—R$^3$—C(O)—NH-collagen+HNZ The reaction can be carried out by dissolving the source collagen in a solvent. The dissolution of the source collagen can be carried out in a two-step process. In the first step, the source collagen may be mixed with methanol. In the second step, a polar aprotic solvent is added. For instance, the source collagen can be added to a mixture of methanol and dimethylsulfoxide, and allowed to swell. Additional dimethylsulfoxide can be added with stirring until dissolution of the source collagen is complete. Methanol can then be removed from the solution by evaporating under reduced pressure. This solubilising process can be used with both atelocollagen and telocollagen.

The activated dicarboxylic acid derivative can then be dissolved in a solvent, particularly an anhydrous polar aprotic solvent, such as dimethylsulfoxide. Since the activated dicarboxylic acid derivative of formula (I) is sensitive to water, the reaction with collagen is preferably carried out in anhydrous polar aprotic solvents, such as dimethylsulfoxide. The activated dicarboxylic acid derivative dissolved in a solvent is then added to the source collagen solution. The carbonyl group of the activated dicarboxylic acid derivative can react with the ε-amino group of the lysine or hydroxylysine residues present in the source collagen to form an amide bond.

The mixture can be stirred at room temperature, for instance 22° C., until a gel is formed. The mixture containing the gel can then be left undisturbed e.g. for 12-18 hr. The dimethylsulfoxide can then be extracted from the gel by blending with an excess of acetone, collecting the collagen gel by decantation and then reblending with more acetone. The mixture can then be stirred e.g. for 0.5 to 1 hr and the collagen subsequently isolated by filtration, washed with acetone, then washed with water-ethanol (30:70 v/v) and dehydrated with ethanol. A collagen comprising a S—S bond is thereby provided, such as a collagen of one or more of Type I, II, III, IV, V, IX and X comprising a S—S bond.

In an alternative embodiment, the collagen comprising a S—S bond may be provided by modifying a collagen-binding protein to include a photoreactive cross-linker comprising a disulphide group, combining this with source collagen to provide a complex and irradiating the complex to cross-link the photoreactive cross-linker to incorporate the disulphide group into the collagen. For instance, the collagen comprising a S—S bond may be collagen of one or more of Type I, II, III, IV, V, VI, IX, X and XI comprising a S—S bond and may be produced from source collagen of one or more of Type I, II, III, IV, V, VI, IX, X and XI.

This route creates protein-binding sites on collagen by using a site-specific photo-cross-linking strategy allowing the creation of thiol groups in collagen. This involves the introduction of a cysteine residue into the collagen-binding protein by site-directed mutagenesis. A photoreactive cross-linker, preferably APDP, can be introduced into cysteine —SH groups on proteins. The complex of APDP-modified protein and collagen can be cross-linked by ultraviolet (uv) irradiation. The disulfide cross-link can then be cleaved by reduction, and an —SH group is generated on collagen allowing for subsequent S-nitrosation.

In a first step, a collagen-binding protein comprising a cysteine residue is provided, as shown in FIG. 1b), step a. A cysteine residue is necessary because this comprises a sulphydryl group necessary for reaction with the cross-linker. The collagen-binding protein may be, for instance, pigment epithelium-derived factor (PEDF). PEDF is a known anti-angiogenic/neurotrophic factor with a collagen binding site identified by Yasui et al as disclosed in *Biochemistry*, 2003, 42, pages 3160-3167.

If necessary, cysteine may be incorporated into the collagen-binding protein if not already present or if the collagen-binding protein does not contain sufficient cysteine. Cysteine substitutions can be made via site-directed mutagenesis, for instance where the collagen binding site is localised (F383) and on the opposite surface of the site (Y211). Methods for carrying out such site-directed mutagenesis are found in *J. D. J. Biol. Chem.* 2002, 277, 4223-4231 and R. R. Biochemistry 1992, 31, 9526-9532.

The sulphydryl groups introduced as a result of the cysteine substitutions can then be reacted with a photoreactive cross-linker as shown in FIG. 1b), step b. The photoreactive cross-linker should be bifunctional. In particular, the photoreactive cross-linker should comprise a functional group capable of reacting with a sulphydryl group to produce a disulphide bond. One such suitable functional group is a pyridyl-dithio group i.e. $C_5NH_5$—S—S—, particularly 2-pyridyl dithio. The photoreactive cross-linker should also comprise a functional group capable of cross-linking with collagen under photo-irradiation. One such suitable functional group is an azide group, particularly an aryl azide group, such as a phenyl azide, especially para —$C_6H_4$—$N_3$.

N-[4-(p-azidosalicylamido)butyl]-3'-(2'pyridyldithio) propionamide (APDP) is one example of a preferred photoreactive cross-linker and its structure is shown in FIG. 1a). The disulphide group of APDP can react with the sulphydryl group of the cysteine to produce a disulphide bond between the cysteine and the photoreactive cross-linker, thereby providing a photoreactive cross-linker modified collagen binding protein comprising a S—S group. 2-pyridyl thione is liberated as part of this reaction as a leaving group.

The photoreactive cross-linker modified collagen-binding protein can then be combined with a collagen, such as collagen of one or more of Type I, II, III, IV, V, VI, IX, X and XI, to provide a complex of the photoreactive cross-linker modified collagen-binding protein and the collagen, as shown in FIG. 1b), step c. In this step, the photoreactive cross-linker modified collagen-binding protein binds to the protein binding site of the collagen to form the complex. The complex of the photoreactive cross-linker modified collagen-binding protein and the collagen can then be irradiated, for example with uv light. Irradiation causes the functional group capable of cross-linking present on the photoreactive cross-linker to form a covalent bond with the adjacent collagen in the complex, as shown in FIG. 1b), step d. For example, when the functional group capable of cross-linking is a phenyl azide, irradiation at a wavelength in the range of from 250 to 280 nm will generate a nitrene, which can then attack nucleophilic or active hydrogen groups, such as C—H or C—$NH_2$ on the collagen to generate a cross-link by insertion across the C—H or N—H bond. In this way, the photoreactive cross-linker modified collagen binding protein comprising a S—S group is incorporated into the collagen to provide collagen comprising a S—S bond. It will be apparent that the disulphide group will be provided in the vicinity of the collagen protein binding site by this route.

A sulphydryl group can then be introduced into the collagen comprising a S—S bond which can be provided by either of the methods discussed above i.e. using the activated dicarboxylic acid derivate or photoreactive cross-linker methods. The collagen comprising a S—S bond can be reacted with a suitable reducing agent, for instance as shown in FIG. 1b), step e. The reducing agent reduces the disulphide bond to two sulphydryl groups, thereby cleaving the activated dicarboxylic acid derivative residue or the photoreactive cross-linker residue, in which the disulphide group is located. Such a reduction proceeds by two sequential thiol-disulphide exchange reactions, resulting in the reduction of the disulphide group to produce collagen comprising a sulphydryl (—SH) group.

Suitable reducing agents include, for example, dithiothreitol (DTT), (2S)-2-amino-1,4-dimercaptobutane (DTBA) and tris(2-carboxyethyl) phosphine HCl (TCEP hydrochloride). Dithiothreitol is a preferred reducing agent.

The reduction step can be carried out by adding the collagen comprising a S—S bond to a buffer solution, such as a glycine/sodium hydroxide buffer solution at a pH of in the range of from 7.5 to 9.5, more preferably about 8 to 9.5, preferably about 8.0. The collagen comprising a S—S bond may be inherently acidic, and if so, neutralisation with a base, such as sodium hydroxide, may be required.

Preferably, at least two molar equivalents of DTT reducing agent can be added per mole of disulphide group in the same buffer and the reaction allowed to proceed at 30° C. for 2-6 hr. After completion of the reaction, the pH of the liquid may be decreased to 2, for instance using HCl. The mixture may then be dialysed with dilute HCl solution, centrifuged and freeze-dried to provide the collagen thiol having a —SH group.

The reduction may cause a slight degradation of the collagen chains. Consequently, shorter reaction times, lower pH and lower temperature can all be used to minimise any degradation.

It will be apparent that when the collagen comprising a S—S bond is provided using a photoreactive cross-linker modified collagen-binding protein, the modified collagen-binding protein will still be attached to the collagen via the photoreactive cross-linker as shown in FIG. 1b), step d prior to the step of forming the collagen thiol. Reduction of the S—S bond will cleave the S—S bond of the photoreactive cross-linker.

When the source collagen comprises one or both of lysine and hydroxylysine residues, a collagen thiol comprising a lysine or hydroxylysine residue of formula (X) is provided:

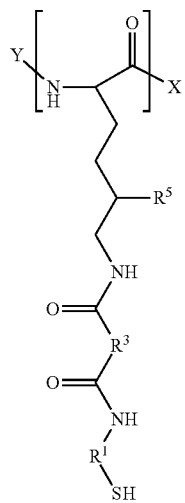

(X)

in which $R^1$, $R^3$ and $R^5$ are as defined above. For instance, $R^1$ and $R^3$ are independently selected from divalent linking groups, preferably divalent organic linking groups, more preferably divalent hydrocarbon linking groups, such as an alkanediyl group having from 1 to 6 carbon atoms or alkendiyl or alkyndiyl groups having from 2 to 6 carbon atoms. Still more preferably, $R^1$ and $R^3$ independently represent ethanediyl or propanediyl groups, most preferably ethanediyl i.e. —$CH_2CH_2$—.
$R^5$ is H when the amino acid residue is a lysine residue.
$R^5$ is OH when the amino acid residue is a hydroxylysine residue;

X is selected from the group OH and a chemical bond and Y is selected from H and a chemical bond, with the proviso that one or both of X and Y are chemical bonds forming peptide bonds within collagen. The peptide chain forming part of the modified collagen is shown bracketed by "[ ]" in formula (X). The residue could be in a terminal position of the peptide, for instance if one or other of X and Y is OH and H respectively. If both X and Y are peptide bonds, the lysine residue is non-terminal within the peptide chain forming part of the collagen.

The collagen thiol having a —SH group can then be nitrosated to provide a modified collagen comprising S-nitroso groups, as shown in FIG. 1b), step f. The S-nitrosation may be carried out by any technique known in the art for the S-nitrosation of proteins. It is preferred that the nitrosation is carried out in the presence of a chelating agent, such as EDTA, in order to improve the stability of the collagen comprising an S-nitroso group product, for instance by eliminating the presence of transition metal ions, which catalyse the decomposition of the S-nitroso group. It is further preferred that the nitrosation is carried out at below room temperature, such as a temperature of less than 5° C., more preferably at a temperature of less than 0° C., in order to minimise any degradation of the S-nitroso product.

For instance, the collagen thiol may be reacted with an aqueous solution of acidified nitrite. The nitrite may be an alkali metal nitrite, such as sodium or potassium nitrite, preferably sodium nitrite. The acidification can be carried out using a buffer, such as phosphate buffered saline. As the nitrosation reaction progresses, hydrogen ions are liberated, leading to an increase in the acidity of the solution which is stabilised by the buffer. Dilute solutions of nitrite salts, when acidified can produce free nitrous acid which react with a sulphydryl group to form a S-nitroso group on the collagen and yield water as a byproduct. Such a reaction is disclosed by Byler D M, Gosser D K, Susi H in a 1983 paper titled 'Spectroscopic Estimation of the Extent of S-Nitrosothiol Formation by Nitrite Action on Sulfhydryl-Groups' in Journal of Agricultural and Food Chemistry 31: 523-527. Wink D A, Nims R W, Darbyshire J F, et al. in 1994 investigated 'Reaction-Kinetics for Nitrosation of Cysteine and Glutathione in Aerobic Nitric-Oxide Solutions at Neutral pH— Insights into the Fate and Physiological-Effects of Intermediates Generated in the NO/O-2 Reaction' in Chemical Research in Toxicology 7: 519-525.

Alternatively, the collagen thiol may be reacted with gaseous NO. This may be achieved my bubbling gaseous NO through the collagen thiol in a solvent. The collagen thiol may also be reacted with a S-nitrosothiol. Preferably, the S-nitrosothiol is a relatively labile and of low molecular weight, such as a gaseous compound. More preferably, the S-nitrosothiol is one or more compounds selected from the group comprising S-nitroso-glutathione, S-nitroso-N-acetyl-penicillamine and S-nitroso-cysteine. Reaction with a S-nitrosothiol may be carried out in a dialysis bag and low molecular weight reagents and products dialyzed out to leave S-nitrosated collagen.

The nitrosation reaction can be monitored spectrophotometrically because of the existence of S—NO specific absorption peaks in the range of 330-340 nm, such as at 339 nm and in the range of 540-600 nm, such as at 545 nm in the uv-visible spectrum. The absorption peaks can be monitored in the presence and absence of $Cu^+$ ions, known to release NO from S-nitrosothiols. Both the generation of NO (by NO electrode) and the reduction in absorbance at a wavelength in the range of from 330-340 nm, such as λ=339 nm is indicative of successful generation of NO release from the S-nitroso collagen.

Similarly, specific absorption peaks in the range of 1480-1530 cm−1 are indicative of the stretching vibration of the N=O bond of a S-nitrosothiol in the infrared spectrum. A second absorption peak in the range of 600-730 cm$^{-1}$ is characteristic of the vibration of the C—S bond in the S-nitrosothiol. When the source collagen comprises one or both of lysine and hydroxylysine residues, a modified collagen comprising a lysine or hydroxylysine residue of formula (IX) is provided:

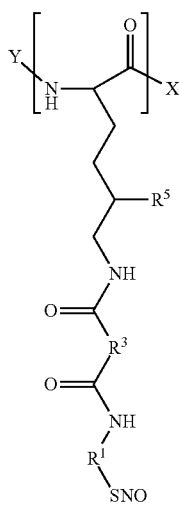

(IX)

in which $R^1$, $R^3$ and $R^5$ are as defined above. For instance, $R^1$ and $R^3$ are independently selected from divalent linking groups, preferably divalent organic linking groups, more preferably divalent hydrocarbon linking groups, such as an alkanediyl group having from 1 to 6 carbon atoms or alkendiyl or alkyndiyl groups having from 2 to 6 carbon atoms. Still more preferably, $R^1$ and $R^3$ independently represent ethanediyl or propanediyl groups, most preferably ethanediyl i.e. —CH$_2$CH$_2$—.
$R^5$ is H when the amino acid residue is a lysine residue. $R^5$ is OH when the amino acid residue is a hydroxylysine residue;
X is selected from the group OH and a chemical bond and Y is selected from H and a chemical bond, with the proviso that one or both of X and Y are chemical bonds forming peptide bonds within collagen. The peptide chain forming part of the modified collagen is shown bracketed by "[ ]" in formula (X). The residue could be in a terminal position of the peptide, for instance if one or other of X and Y is OH and H respectively. If both X and Y are peptide bonds, the lysine residue is non-terminal within the peptide chain forming part of the modified collagen.

When the modified collagen comprises a lysine or hydroxylysine residue comprising a S-nitroso group, such as those discussed above, for instance modified collagen comprising a residue of formula (IX), improved stability of the S-nitroso group to decomposition is observed. For instance, modified collagen comprising a lysine or hydroxylysine residue comprising a S-nitroso group exhibits an approximately 10-fold increase in stability compared to cysteine residues comprising a S-nitroso group.

The modified collagen comprising a S-nitroso group product may be purified, for instance by dialysis. It is preferred that the modified collagen is dialysed against a phosphate buffer comprising ethylene diamine tetraacetic acid (EDTA) in water.

In another embodiment, the modified collagen described herein may be incorporated into a one or more of the group comprising a type II collagen, a type V collagen and a gelatin matrix. Preferably, the collagen is derived from a jellyfish, such as *Rhizostoma pulmo* jellyfish tissue i.e. Barrel jellyfish.

The modified collagen described herein may be for use as a medicament.

In one embodiment, the modified collagen is for use in wound healing. Thus, also disclosed herein is a method of treatment of a wound in an individual, comprising at least the step of attaching a modified collagen as described herein to the wound. The modified collagen may be attached by any conventional means, such as binding e.g. as part of a wound dressing, gluing, suturing etc. The wound may be an ulcer, such as a diabetic ulcer, for instance a diabetic foot ulcer.

Formulation of the modified collagen for maximum delivery of localised and controlled release of NO to support beneficial clinical effects can be either delivered in a gel matrix (e.g. extracellular matrix) form or more preferably formulated into any suitable polymer material scaffold made or composed of one or more of collagen, gelatine, hyaluronic acid, polymethylcellulose, alginate, alginic acid and silicone based materials.

There is also provided a wound dressing comprising a formulated composition comprising the modified collagen described herein incorporated into one or more of the group comprising a type II collagen derived from a jellyfish, a type V collagen derived from a jellyfish and a gelatin matrix.

Preferably, when the collagen is derived from a jellyfish it is derived from *Rhizostoma pulmo* jellyfish tissue i.e. Barrel jellyfish.

The formulated composition of the wound dressing may be a film, membrane or hydrogel composite. Preferably, the wound dressing has a thickness in a range of from 5 to 200 micrometers. As used herein the term 'thickness' refers to the smallest dimension of the wound dressing.

The wound dressing may further comprise food grade agents.

The wound dressing may further comprise medical grade agents.

It is preferred that the film, membrane or hydrogel composite is sterilised, preferably during formation of the wound dressing. The sterilisation may be achieved using filter sterilisation, such as with a filter in the range of from 0.22 μm to 0.45 μm or by treatment with Ethylene Oxide (EtO) or by gamma irradiation.

The wound dressing is preferably stored below room temperature, preferably at a temperature below 4° C. The wound dressing is preferably stored under anhydrous conditions. The wound dressing is preferably stored under an inert atmosphere, such as under nitrogen. These steps minimise decomposition of the S-nitroso groups.

The wound dressing disclosed herein provides enhanced vasodilation effects with respect to blood flow control due to the presence of the S-nitroso groups of the modified collagen. The S-nitroso groups can release nitric oxide under physiological conditions. Nitric oxide is known to provide vasodilation effects.

In another embodiment, the wound dressing acts as an effective disinfection agent. Endogenously produced nitric oxide is an important component of the body's natural defence mechanism. Depending on its concentration, NO exerts antimicrobial effects in two ways. At low concentrations, NO acts as a signalling molecule that promotes the growth and activity of immune cells. At high concentrations, such as during the respiratory burst of a neutrophil, NO covalently binds DNA, proteins and lipids, thereby inhibiting or killing target pathogens. Considering that NO is an integral and highly conserved part of the host immune response, it is not surprising that few bacteria are able to escape the antimicrobial effect of NO.

In another embodiment, the wound dressing is antimicrobial. In particular, the wound dressing exhibits antimicrobial properties against bacteria, yeasts, fungi and viruses. This is because the nitric oxide released by the S-nitroso groups of the modified collagen exerts antimicrobial activity.

Various further aspects and embodiments of the present invention will be apparent to those skilled in the art in view of the present disclosure.

Other aspects and embodiments of the invention provide the aspects and embodiments described above with the term "comprising" replaced by the term "consisting of" and the aspects and embodiments described above with the term "comprising" replaced by the term "consisting essentially of".

EXPERIMENTAL

The following experimental example describes the synthesis of a modified collagen comprising S-nitroso groups from a jellyfish source. The half-life of the modified collagen comprising S-nitroso groups is also investigated.

The collagen source was obtained from a barrel jellyfish, *Rhizostoma pulmo*. A 1.003 g sample of jellyfish collagen (comprising collagen derived from mesogloea and oral arms) were first enzyme digested by addition of from 0.1% to 0.001% v/v pepsin (Sigma) to provide atelocollagen. Firstly, a pepsin enzyme stock solution of 10 mg/ml was made in 0.1 M acetic acid and mixed on a vortex then stored at 4° C. This enzyme stock solution was added until a final concentration of from 0.1% to 0.001% v/v was reached, more preferably a final concentration of 0.01% v/v pepsin. All enzyme collagen digest samples were stored at 4° C.

The atelocollagen was then swelled in 200-400 mL methanol (Rathburn Chemicals Ltd.). The swollen atelocollagen did not dissolve after stirring for 1 hr.

In order to dissolve the swollen atelocollagen, 40 mL dimethylsulfoxide (Rathburn Chemicals Ltd.) was added and the mixture stirred for 20 minutes with 1 minute sonication. A further 200-450 mL dimethylsulfoxide was added and the mixture stirred for 1 hr with intermittent sonication for periods of 30 s to provide an atelocollagen solution in dimethylsulfoxide.

The methanol was removed from the atelocollagen solution under reduced pressure at a temperature of 35° C.

A 400 mg sample of N,N'-disuccinoyl cystamine dissolved in 16 mL dimethylsulfoxide was added to the atelocollagen solution, which was then covered and stirred 2.5 hrs.

The mixture was then allowed to stand for 16 hrs after which a yellow liquid with a strong odour was obtained. There was no change to the viscosity.

The atelocollagen comprising an S—S bond was then blended with acetone (Brenntag) in a ratio of 2:1 v/v acetone:atelocollagen mixture. An off-white, flaky precipitate was formed after 30 seconds on the first blend. The blend was left to stand for 1 hr at a temperature of <10° C., preferably at a temperature of 2-5° C., after which the settling of some precipitate was observed, with the rest of the particles remaining in suspension.

The atelocollagen comprising an S—S bond was collected by centrifugation and removal of supernatant. The blending with acetone, settling and centrifugation was repeated two further times in order to complete precipitation.

The atelocollagen comprising an S—S bond precipitate was then filtered and washed with acetone. The precipitate collected by gravitational filtration using glass fibre filter paper with a pore size of 1.6 μm. The precipitate was washed five times with 100 mL acetone to yield a thick yellow-brown gel-like material.

The atelocollagen comprising an S—S bond precipitate was then rinsed with 100 mL 70:30 v/v denatured ethanol (Sigma)/water which resulted in the precipitate coalescing together to form an elastic-like, grey-brown material.

After the denatured ethanol wash, the coalesced precipitate was freeze-dried to provide 375 mg of an off-which chalk-like atelocollagen comprising an S—S bond.

The freeze-dried atelocollagen comprising an S—S bond was mixed with 50 mL of 0.1 M glycine/NaOH buffer having a pH of 9.5. After vortexing and vigorous shaking a yellow-brown gel-like material was formed.

To this collagen mixture, of dithiothreitol (Sigma) was added and the pH fell to 8.04. The atelocollagen completely dissolved after stirring for 4 hr to yield a more viscous, pale peach solution of atelocollagen comprising an S—H group (compound of formula (X) in which $R^1$ and $R^3$ are —$CH_2CH_2$— and $R^5$ is H).

The atelocollagen comprising an S—H group was then dialysed with 18 mM HCl (Fischer Scientific). The dialysis was repeated once with fresh dialysis medium. There was no change in the consistency of the liquid after 24.5 hrs.

The dialysed atelocollagen comprising an S—H group was then centrifuged to provide a pellet of a solid modified collagen and a pale yellow fibrous supernatant.

A 343 mg sample of the atelocollagen comprising an S—H group was then added to 5 mL phosphate buffered saline (Fischer Scientific) to form a gelatinous ball having a total weight of 5.34 g. A 0.4313 g sample of the gelatinous ball was cut and chopped into a glass universal vial, then dissolved in 2 ml chelex treated $H_2O$ in a water bath at 37° C. The solution had a pH of 2.19.

Prior to nitrosation, 40 μM EDTA (Sigma) was added.

The sample was then split into 2 aliquots, the first kept at room temperature, and the second chilled with ice.

A 0.003 g sample of 40 mM sodium nitrite (Sigma) was added to each aliquot to initiate nitrosation process. The mixtures were wrapped foil to eliminate light. Both aliquots became visibly rose pink within 2.5 minutes.

Aliquot a) was examined on Variskan plate reader over a range wavelength of 290 to 450 nm at 5, 10, 20, 30, 60 and 90 minutes. FIG. 2 shows the absorption spectrum for the sample at 10 minutes. A control plate to which no sodium nitrite had been added was also examined and the spectrum is also shown in FIG. 2. It is apparent that the spectrum for the nitrite treated sample at 10 minutes shows a significant absorption peak at around 335 nm, indicative of S-nitroso formation.

Aliquot b) on ice became extremely viscous and so samples could not be pipetted into a well plate. The colour remained vivid however and at 60 minutes the sample was warmed in the water bath to return it to its fluid state again.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

The invention claimed is:

1. A modified collagen comprising S-nitroso groups obtainable by the method comprising at least the steps of:
   providing a collagen comprising a S—S bond, wherein the source of the collagen is one or more selected from the group consisting of jellyfish, marine invertebrates, and fish;
   introducing a —SH group in said collagen comprising a S—S bond by reduction of the S—S bond to provide a collagen thiol comprising a SH group;
   nitrosating the SH group of the collagen thiol to provide a modified collagen, said modified collagen comprising one or both of lysine and hydroxylysine residues comprising S-nitroso groups,
wherein the one or both of the lysine and hydroxylysine residues is represented by the formula (IX):

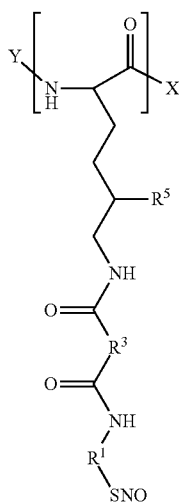

(IX)

in which $R^1$ and $R^3$ are independently divalent linking groups;
$R^5$ is H or OH;
X is the group OH or a chemical bond; and
Y is H or a chemical bond, with the proviso that one or both of X and Y are chemical bonds forming peptide bonds within the modified collagen.

2. The modified collagen according to claim 1 for use as a medicament.

3. The modified collagen according to claim 1 for use in wound healing.

4. A wound dressing comprising a formulated composition comprising the modified collagen according to claim 1 and a gelatin matrix, wherein the collagen is one or more selected from the group consisting of a type I collagen derived from a jellyfish, a type II collagen derived from a jellyfish, and a type V collagen derived from a jellyfish.

5. The wound dressing of claim 4, wherein said collagen derived from a jellyfish comprises *Rhizostoma pulmo* jellyfish tissue.

6. The wound dressing of claim 4, further comprising food grade agents or medical grade agents.

7. The wound dressing of claim 4 for use as a vasodilation agent or for use as a disinfection agent.

8. The wound dressing of claim 7 having antimicrobial properties against bacteria, yeasts, fungi and viruses.

9. A wound dressing comprising a formulated composition comprising the modified collagen according to claim 1 incorporated into any polymer matrix.

10. The wound dressing of claim 9 where said formulated composition is a film, membrane or hydrogel composite.

11. The wound dressing of claim 10 wherein said film, membrane or hydrogel composite has a thickness in a range of from 5 to 1000 micrometer.

12. The wound dressing of claim 10, wherein said film, membrane or hydrogel composite is sterilized.

13. The wound dressing of claim 10, wherein said film, membrane or hydrogel composite has a porous structure.

14. The modified collagen of claim 1, wherein the source of collagen comprises one or more of Type I, II, III, IV, V, VI, IX, X and XI collagen comprising a S—S bond.

15. A modified collagen comprising one or both of lysine and hydroxylysine residues comprising S-nitroso groups, wherein the source of the collagen is one or more selected from the group consisting of jellyfish, marine invertebrates, and fish, wherein the one or both of the lysine and hydroxylysine residues is represented by the formula (IX):

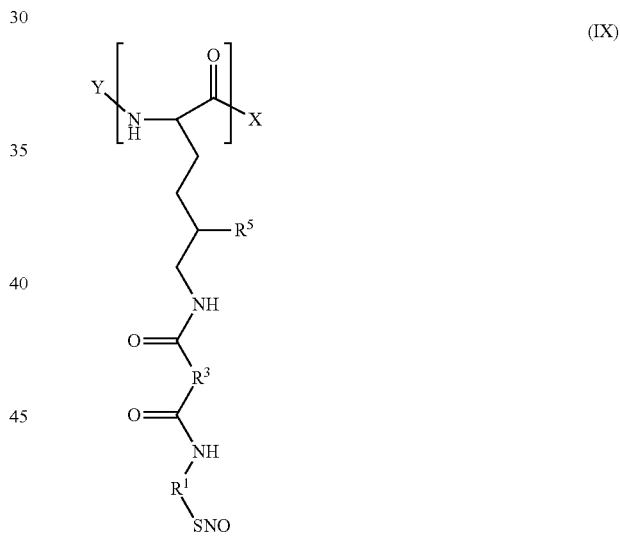

in which $R^1$ and $R^3$ are independently divalent linking groups;
$R^5$ is H or OH;
X is the group OH or a chemical bond; and
Y is H or a chemical bond, with the proviso that one or both of X and Y are chemical bonds forming peptide bonds within the modified collagen.

16. The modified collagen of claim 15, wherein the collagen comprises one or more of Type I, II, III, IV, V, VI, IX, X and XI.

* * * * *